United States Patent
Cronvall

(10) Patent No.: US 8,618,484 B2
(45) Date of Patent: Dec. 31, 2013

(54) FLUID FILM INDICATOR

(75) Inventor: Leif Cronvall, Kivik (SE)

(73) Assignee: Microfluid AB, Lund (SE)

( * ) Notice: Subject to any disclaimer, the term of this patent is extended or adjusted under 35 U.S.C. 154(b) by 0 days.

(21) Appl. No.: 13/122,860

(22) PCT Filed: Oct. 5, 2009

(86) PCT No.: PCT/SE2009/051104
§ 371 (c)(1),
(2), (4) Date: May 11, 2011

(87) PCT Pub. No.: WO2010/042029
PCT Pub. Date: Apr. 15, 2010

(65) Prior Publication Data
US 2011/0204238 A1   Aug. 25, 2011

(30) Foreign Application Priority Data
Oct. 9, 2008 (SE) ........................ 0850034

(51) Int. Cl.
*G01J 5/02* (2006.01)

(52) U.S. Cl.
USPC ............... 250/339.11; 250/339.12; 250/341.8

(58) Field of Classification Search
USPC .............. 250/339.11, 339.12, 341.8
See application file for complete search history.

(56) References Cited

U.S. PATENT DOCUMENTS

| 4,167,746 | A | * | 9/1979 | Storm ........................... 257/115 |
| 4,565,450 | A | * | 1/1986 | Wirz et al. .................... 356/402 |
| 4,575,244 | A | * | 3/1986 | Kaffka et al. ................. 356/343 |
| 4,978,962 | A |   | 12/1990 | Hisada et al. |
| 5,124,552 | A |   | 6/1992 | Anderson |
| 5,302,823 | A |   | 4/1994 | Franklin et al. |
| 5,552,604 | A | * | 9/1996 | Sting et al. ................. 250/341.2 |
| 5,963,333 | A | * | 10/1999 | Walowit et al. ............... 356/425 |
| 6,271,523 | B1 | * | 8/2001 | Weaver et al. ............. 250/341.8 |
| 6,287,871 | B1 | * | 9/2001 | Herron et al. ................. 436/172 |
| 6,424,416 | B1 |   | 7/2002 | Gross et al. |
| 7,538,871 | B2 |   | 5/2009 | Frick et al. |
| 2004/0003739 | A1 | * | 1/2004 | Leif .............................. 101/484 |
| 2006/0244907 | A1 | * | 11/2006 | Simmons ..................... 351/162 |

FOREIGN PATENT DOCUMENTS

| AU | 768800 B2 | 9/2001 |
| EP | 0652423 A1 | 5/1995 |
| EP | 1036828 A1 | 9/2000 |
| JP | 05312723 | 11/1993 |
| JP | 06504126 | 5/1994 |
| JP | 08292147 | 11/1996 |
| JP | 11269790 | 10/1999 |
| JP | 2003513236 | 4/2003 |
| JP | 2006227012 | 8/2006 |
| WO | WO 83/02326 | * 7/1983 ............ G01N 21/17 |
| WO | 0242077 A1 | 5/2002 |

* cited by examiner

*Primary Examiner* — David Porta
*Assistant Examiner* — Kenneth J Malkowski
(74) *Attorney, Agent, or Firm* — Capitol City TechLaw

(57) ABSTRACT

An apparatus for radiometric measurement of thin fluid films includes a housing (1) enclosing means of radiation, a radiation guide, a reflector (4) and one or more detectors (5). The means of radiation is normally an IR radiator (2). The radiation guide is either a radiation tube (3) or a radiation cone (7). The reflector (4) is of the type non-imagining optics. If there is more than one detector (5) normally at least one detector is a reference detector.

11 Claims, 2 Drawing Sheets

FLUID FILM INDICATOR

TECHNICAL FIELD

The present invention concerns an apparatus for radiometric measuring of thin fluid films.

The apparatus of the present invention may for instance use the measuring principal described in WO 02/42077.

BACKGROUND

It is known that different substrates absorb different, specific bands of IR (infrared) radiation. Thus, by directing IR radiation towards a thin film of the substrate it is possible to determine the thickness of the film. By a radiometric analysis it is further possible to determine the proportion of ingredients in the substrate and by continuous monitoring it is possible to establish changes of said proportion. Radiometric analysis is based on the change of energy or absorption of radiation, which in this case has wave-lengths within the IR area.

In many applications it is important to be able to control the thickness of a fluid film and the amount of different ingredients of the fluid film. This control could be used to optimize the desired effect, reduce the amount of used fluid and thereby save costs. In many instances it is normal to use superfluous amounts of a fluid, to be on the safe side. Controlling and monitoring the actual amount of fluid and its ingredients may diminish such superfluous amounts.

SUMMARY

The apparatus of the invention is designed to control and monitor fluid films using absorption of radiation having wavelengths within the IR area. This is done by using the main or other absorption bands of a fluid to be measured and using the change of energy when the radiation passes through a thin fluid film.

The apparatus of the invention may be used for measurement and control of any thin fluid film. Different applications include but are not limited to: printing ink and fountain solution in printing presses; oil films often used in pressing of sheet metal; coatings on paper or metal; and photographic films on substrates within the semiconductor industry.

One object of the present invention is to provide an apparatus that is relatively compact and, thus, easy to install in different environments. In many situations it is an advantage if it could be used as a part of a modular system.

According to the invention an apparatus for radiometric measurement of thin fluid films is provided. The apparatus has a housing enclosing means of radiation, a radiation guide, a reflector and one or more detectors.

Further objects and advantages of the present invention will be obvious to a person skilled in the art reading the detailed description below of different embodiments.

BRIEF DESCRIPTION OF THE DRAWINGS

The invention will be described more closely below by way of example and with reference to the enclosed drawings. In the drawings.

DETAILED DESCRIPTION OF DIFFERENT EMBODIMENTS

Figure 1:
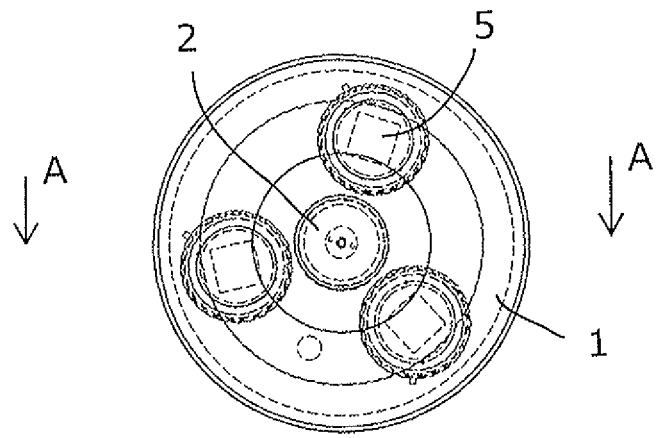
FIG. 1 shows a plan view of an apparatus according to one embodiment of the present invention.

The apparatus of the invention has generally a housing 1. Inside the housing 1 there is at least one radiator 2, a radiation guide 3, 7, guiding the radiation towards a fluid film to be Imonitored, and a reflector 4, directing reflected radiation towards one or more detectors 5 inside the housing 1.

In the different Figs. corresponding parts are given the same reference signs, as long as they have the same general design.

Figure 2:
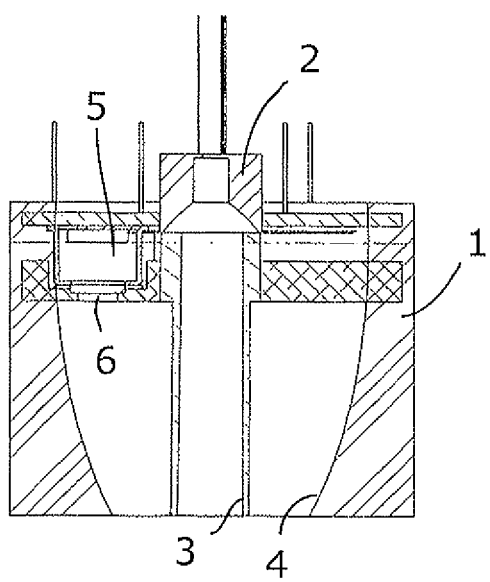
FIG. 2 shows a cross section of the apparatus of FIG. 1 taken along the line A-A.

The housing 1 shown in FIGS. 1 and 2 has a generally cylindrical outer form. In the centre of the housing and at the top an IR radiator 2 is placed. The IR radiator 2 is a wide-band radiator. The IR radiator 2 is modulated with a fixed frequency and the radiation is normally pulsated. The effect of the IR radiator 2 should be high enough to get a reasonable measuring signal.

It is also possible to furnish the apparatus with a small-band radiator. A small-band radiator will give higher flux of radiation energy and a small-band radiator is more energy saving than a wide-band radiator. It is possible to increase the frequency of pulsation which gives increased sensitivity of the detectors.

The IR radiator 2 radiates down into a radiation guide, which in this case is a radiation tube 3. The radiation tube 3 has a generally cylindrical form. By means of the radiation tube 3 the radiation is controlled in such a way that the radiation beams will be parallel when leaving the radiation tube 3, as schematically shown in Fig, 4. Non-parallel radiation beams are extinguished in that they will not reflect from the inner surface of the radiation tube 2. The inner surface of the radiation tube is made or treated to be non-reflective. The radiation of the radiator 2 is led by means of the radiation tube 3 toward a surface on which a fluid film passes and on which fluid film the measurement is to be performed. Normally, the apparatus of the present invention is placed in an active production line and, thus, the control and monitoring of the fluid film is made with a machine etc. running. The surface receiving the fluid film should have a certain reflectance in order for the apparatus to function in the desired way. If the reflectance is to low there could be problems picking up signals at the passage of the fluid film. In such cases the fluid film may be taken out and led to a surface giving enough reflectance.

The radiation is reflected in a scattered way from the surface and is directed by the reflector 4 towards the one or more detectors 5. The reflector 4 is of the type non-imaging optics. The surface of reflector 4 has the shape of a part of an ellipsoid. Thus, seen in cross section the reflector has sides in the form of a part of an ellipse.

In practice each detector 5 may in some cases be formed of an assembly of smaller detectors. For ease of description the term "detector" as used herein is intended to cover both a single detector and an assembly of detectors acting as one unit.

The detectors 5 each have a filter 6. The detectors 5 are so-called wide-band detectors and band-pass filters 6 are placed in front of the detectors. Normally, one detector 5 has a filter 6 letting radiation of a wavelength absorbed by the fluid film through and another detector 5 (reference detector) has a filter 6 letting a wavelength through which does not belong to the absorption band of the fluid film. The relationship between the signal levels picked up by the detectors 5 reflects the thickness of the fluid film. By means of the reference detector it is also possible to compensate for instance for alternating physical properties of the fluid film or the surface which the fluid film passes, the distance to the fluid film and possible background radiation. The apparatus as shown is axially symmetric, thus, the detectors 5 are evenly distributed around a centre line. The detectors 5 are placed at the thickest part of the part of the ellipsoid formed by the reflector 4. The radiation flow is relatively even at that position. By changing filters 6 the apparatus is adapted to different measuring processes, whereby the filter 6 chosen depends on the fluid film to be analyzed.

To save costs and in situation where the conditions are relatively stable it may suffice to use only one single detector 5. Thus, in such a case there is no reference detector.

Figure 3:
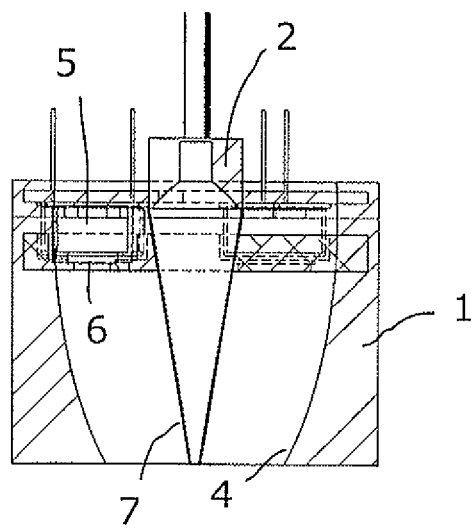
FIG. 3 shows a cross section corresponding to FIG. 2 of an alternative embodiment.
Figure 4:
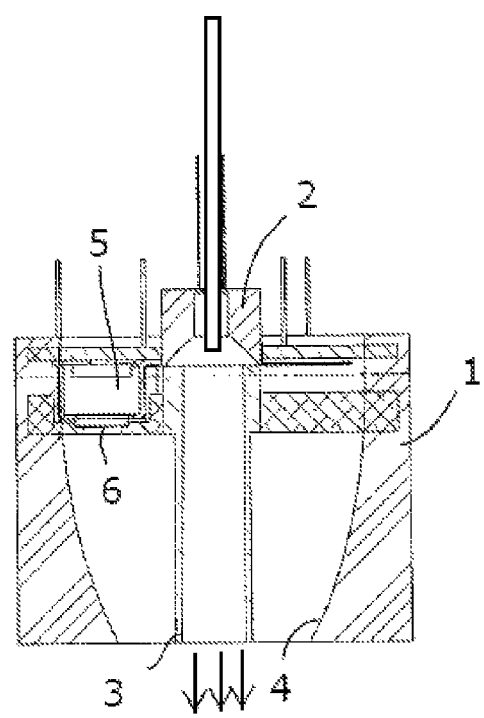
FIG. 4 shows a cross section of the apparatus of Fig. I taken along the line A-A. and schematically showing parallel radiation beams.

The only difference between the embodiments of FIG. 3 and FIG. 2 is that the radiation guide of the embodiment of FIG. 3 is a radiation cone 7. By use of the radiation cone 7 the radiation hitting the fluid film will be more concentrated.

In an alternative embodiment the apparatus has a rectangular outer appearance, whereby normally two detectors are placed in-line with each other on opposite sides of the IR radiator. In this case the reflector will have two opposite surfaces having the cross section form of a part of an ellipse and two opposite surfaces having a straight cross section form. By using a rectangular outer form it is relatively easy to give the apparatus of the invention a modular structure.

An axially symmetric apparatus may have any suitable number of detectors. An apparatus having a rectangular outer dimension will normally only have two detectors. In some cases an apparatus having a rectangular outer dimension will have more than two detectors, which detectors not necessarily are placed in-line. By using several detectors it will be possible for instance to measure the concentrations of different parts of the fluid film.

In one embodiment there is a glass window between the apparatus and the fluid film, which window is transparent for the wavelengths concerned. There may also be a so-called air knife, transporting away particles and splashes from the measuring process. Thus, both a possible glass window and air knife will protect the apparatus in tough environments.

Normally electronics to control the different parts, to evaluate the measurements and to possibly amplify signals are placed inside the housing 1 of the apparatus. However, a person skilled in the art realises that these parts may be placed outside the housing, and the communication with these parts may either be through a wire or wireless.

In a further alternative embodiment fibre optic is used to lead for instance light of a laser towards the fluid film. Hereby a fibre optic cable is received inside the radiation guide. By placing the fibre optic cable at the top of the radiation guide non-parallel radiation beams leaving the fibre optic cable will not be reflected on the inner surface of the radiation guide.

The invention claimed is:

1. An apparatus for radiometric measurement of thin fluid films, the apparatus comprising:
   a housing;
   at least one radiator provided in the housing, the at least one radiator configured to emit radiation beams;
   a radiation tube configured to lead the radiation beams from the radiator towards the fluid film to be measured, the radiation tube configured to control the radiation beams to be parallel; and
   a non-imaging reflector configured to direct reflected radiation beams towards one or more detectors provided inside the housing;
   wherein the non-imaging reflector is situated between the one or more detectors and the fluid film to be measured;
   wherein the radiation tube extends along an axis of the non-imaging reflector, and into the interior of the non-imaging reflector: and
   wherein the radiation tube has an inner surface that is non-reflective.

2. The apparatus of claim 1, wherein the radiator is an IR radiator.

3. The apparatus of claim 2, wherein the radiation tube is placed directly under the IR radiator.

4. The apparatus of claim 1, wherein a fibre optic cable is used to lead the radiation beams to the radiation tube.

5. The apparatus of claim 1, wherein the non-imaging reflector has the form of a part of an ellipsoid.

6. The apparatus of claim 1, wherein the non-imaging reflector has two opposite sides with a straight cross section form and two opposite surfaces with a cross section form as a part of an ellipse.

7. The apparatus of claim 1, wherein the housing has an outer cylindrical form.

8. The apparatus of claim 1, wherein the housing has an outer rectangular form.

9. The apparatus of claim 1, wherein at least two detectors are provided inside the housing, of which at least one is a reference detector.

10. The apparatus of claim 1, wherein the non-imaging reflector is provided inside the housing.

11. The apparatus of claim 1, wherein a characteristic of the film to be measured is the thickness of the film.

* * * * *